(12) United States Patent
Wang et al.

(10) Patent No.: US 11,712,042 B2
(45) Date of Patent: Aug. 1, 2023

(54) **HIGH ESTERS PRODUCING STRAIN OF *MONASCUS PURPUREUS* AND ITS APPLICATION IN PRODUCTION OF ESTER FLAVOR *MONASCUS* FERMENTED CHEESE**

(71) Applicant: Beijing Technology and Business University, Beijing (CN)

(72) Inventors: Bei Wang, Beijing (CN); Zhijie Yang, Beijing (CN); Jing Wang, Beijing (CN); Jinhua Zhang, Beijing (CN); Ye Liu, Beijing (CN); Zhennai Yang, Beijing (CN); Duoxia Xu, Beijing (CN)

(73) Assignee: BEIJING TECHNOLOGY AND BUSINESS UNIVERSITY, Beijing (CN)

( * ) Notice: Subject to any disclaimer, the term of this patent is extended or adjusted under 35 U.S.C. 154(b) by 132 days.

(21) Appl. No.: 17/152,102

(22) Filed: Jan. 19, 2021

(65) Prior Publication Data

US 2021/0219564 A1 Jul. 22, 2021

(30) Foreign Application Priority Data

Jan. 19, 2020 (CN) .......................... 202010059852.3

(51) Int. Cl.
*A23C 19/032* (2006.01)
*A23C 19/08* (2006.01)
(Continued)

(52) U.S. Cl.
CPC .......... *A23C 19/0325* (2013.01); *A23C 19/08* (2013.01); *C12N 1/145* (2021.05); *C12R 2001/645* (2021.05)

(58) Field of Classification Search
CPC ... A23C 19/0325; A23C 19/08; A23C 19/061; A23C 19/14; C12N 1/145; C12N 3/00; C12R 2001/645; A23L 27/25
See application file for complete search history.

(56) References Cited

FOREIGN PATENT DOCUMENTS

| CN | 104585333 A | * | 5/2015 |
| CN | 206153020 U | | 5/2017 |

(Continued)

OTHER PUBLICATIONS

Translation of CN-107691657-A, "Preparation method of red soft cheese and product made by preparation method". (Year: 2018).*

(Continued)

*Primary Examiner* — Donald R Spamer
*Assistant Examiner* — Jeffrey D Benson
(74) *Attorney, Agent, or Firm* — Edwin S. Flores; Daniel J. Chalker; Chalker Flores, LLP

(57) ABSTRACT

The invention discloses a strain of *Monascus purpureus* with high esters producing activity and the application in the production of ester flavored *Monascus* cheese. The strain was deposited in China General Microbiological Culture Collection Center (CGMCC) on Oct. 17, 2019, with the preservation number of CGMCC 18589. The strain can make the cheese flavor having less pungent, and richer, significantly improve the odor quality of cheese, thus more in line with the taste of Chinese people. Moreover, some secondary metabolites responsible for health benefits including hypolipidemia, antihypertensive, antioxidant, and antihyperglycemic effects and prevention of obesity and diabetes development have been recognized in *Monascus*-fermented cheese.

9 Claims, 2 Drawing Sheets

(51) Int. Cl.
*C12R 1/645* (2006.01)
*C12N 1/14* (2006.01)

(56) References Cited

FOREIGN PATENT DOCUMENTS

CN 106894472 A 6/2017
CN 107691657 A * 2/2018 ........... A23C 19/032

OTHER PUBLICATIONS

Translation of CN104585333A, "Monascus cheese, monascus purpureus and culture method of monascus purpureus" (Year: 2015).*
Office Action CN 2020100599852.3 dated Jul. 2, 20218 and English Translation.
Wu, Shenmao et al. "Influence of Monascus purpureus BD-M-4 on the physicochemical properties, proteolysis and volatile compounds of surface mould-ripened cheese" Food Sci Biotechnol (2019) 28(1):129-138.

* cited by examiner

HIGH ESTERS PRODUCING STRAIN OF *MONASCUS PURPUREUS* AND ITS APPLICATION IN PRODUCTION OF ESTER FLAVOR *MONASCUS* FERMENTED CHEESE

CROSS-REFERENCE TO RELATED APPLICATIONS

This application claims priority to China Application Serial No. 202010059852.3, filed Jan. 19, 2020, the entire contents of which are incorporated herein by reference.

TECHNICAL FIELD

The invention belongs to the field of microorganism and food processing, in particular to a strain of *Monascus purpureus* with high esters producing activity and its application in the cheese producing.

BACKGROUND ART

Cheese is a kind of fresh or fermented dairy product which is made of pasteurized fresh milk, chymosin and starters. Cheese is rich in protein, fat, a variety of amino acids, vitamins and minerals, which is equivalent to concentrate fresh milk about 10 times. It is a fermented dairy product with high nutritional value. Eating cheese is helpful to reduce the serum cholesterol and prevent cardiovascular disease. Cheese contains almost no lactose or the content is very low. It is especially suitable for diabetes and the consumers with lactose intolerance. Cheese contains calcium, phosphorus and other essential minerals for human body. Every 100 g soft cheese can meet 30%-40% of the daily calcium demand of adults, and every 100 g of hard cheese can fully meet the daily calcium demand and 40%-50% of the daily phosphorus demand. Cheese is rich in fat soluble vitamins, nicotinic acid, folic acid, biotin and so on.

With the gradual familiarity and acceptance of cheese, people pay more and more attention on it. It is well-known that cheese flavor is the key factor affecting the quality of cheese, which is mainly composed of volatile flavor components and taste components. Among them, fatty acids have an important impact on cheese flavor, not only they are flavor substances, but also they are the precursors of esters, methyl ketone, alcohol, lactones and other flavor substances in cheese. Among the fatty acids, butyric acid has a strong pungent odor, caproic acid has a rotten smell, octanoic acid presents soap and putrid butter smell, decanoic acid has unpleasant fat smell. These four fatty acids give cheese a pungent and rancid flavor profile which lead to the main reason of cheese dislike of Chinese customers.

Based on some studies, the regional differences of flavor characteristics of commercial Cheddar cheese and the preference of consumers for the flavor characteristics of Cheddar cheese were analyzed. The results showed that the preference sensory differences of Cheddar cheeses with different producers were mainly due to their volatile acids. Consumers prefer milk flavor and nut flavor of Cheddar cheese, while Cheddar cheese with high pungent smell, sulfur smell and bitter taste is not welcomed by most consumers. Therefore, it is more suitable for Chinese consumers to develop cheese with heavy milk flavor and strong nut flavor. Moreover, esters, such as ethyl butyrate with some special milky, floral, fruity and wine aroma can be well covered unpleasant smell caused by fatty acids in cheese. Therefore, increasing ester compounds contents in cheese can improve the cheese sensory quality.

As for the, there were some Chinese studies about *Monascus* fermented cheese Lu Xiaobin et al. (paper entitled Application of *Monascus* in cheese production. Science and Technology of Food Industry, 2003 (05): 61-62) found out the optimal production process conditions of *Monascus* fermented cheese with high cheese yield. In another study (Sun Yanjun, sun Yanjie. Application of *Monascus* in Cambert like cheese production. Food industry science and technology, 2016, 37 (13): 167-172), a *Monascus* strain with high pigment production and no citrinin production was isolated from traditional Chinese *Monascus* fermented food to replace white mold in Camembert cheese manufacturing.

Chinese patent applications (201310342818.7, 201310343137.2 and 201310343139.1) disclose some preparation method of *Monascus* cheese, in which the steps of spraying or smearing the mixture of *Monascus* fermentation broth and acidified rice paste on the surface of curd. Anther Chinese patent application (201410723647.7) discloses a strain of *Monascus* with high yield of γ-aminobutyric acid. The *Monascus* strain was used as a starter to make *Monascus* cheese, which can enhance the healthy function of the product. The application of *Monascus* cheese in those papers and patents endow the mold cheese with new product characteristics. These *Monascus* fermented cheeses are better than traditional cheese in appearance and nutrition, however, there is no significant improvement in cheese flavor and their own pungent odor are still relatively strong.

SUMMARY OF THE INVENTION

The *Monascus purpureus* strain with high esters producing activity was selected by special screening and mutation. The *Monascus* strain could metabolize a large number of fatty acid compounds in cheese fermentation process into ester components. These short chain fatty acid esters, such as ethyl butyrate, have strong milky or fruity flavor. Ester compounds can not only give the product a special ester flavor (similar to floral and fruity), but also can further decrease the pungent flavor caused by the high concentration of medium and short chain fatty acids. Thus, giving sample a gentler aroma profile. In addition, there are also have some extra methyl ketones in *Monascus* fermented cheese. These compounds mainly make the cheese have a more complex pleasant flavor, and give a positive effect on the overall flavor of cheese. *Monascus* strains with high esters producing acidity can significantly improve both aroma and nutrition quality of cheese, it has an important application prospect.

Therefore, the invention first provides a *Monascus purpureus* strain with high ester producing activity, which was deposited in China General Microbiological Culture Collection Center (CGMCC) on Oct. 17, 2019, with the preservation number of CGMCC 18589, preservation address: 3 Beichen West Road, Chaoyang District, Beijing.

Secondly, the invention provides the application in the production of the mutant *Monascus purpureus* strain cheese with high esters production.

Thirdly, the invention provides a manufacturing process of *Monascus* fermented cheese, which comprises the following steps:

(1) preparation of the cheese curd with starter and chymosin;

(2) inoculation the spore of *Monascus purpureus* with high esters producing activity according to claim 1;

(3) keeping the cheese curd in constant temperature to make the *Monascus* grow better;

(4) cheese ripening.

According to the step (1), the production process of *Monascus* fermented cheese comprises cutting the cheese curd into thin slices and vertically penetrating some holes.

The specific operation of step (2) is to prepare a suspension of the spores of *Monascus purpureus* and then inject it into the holes in cheese curd.

The optimum cultivation temperature of step (3) is 25-35° C., and the cultivation time is 2-4 days, 3 days is better.

The production process of *Monascus* fermented cheese mature, which is characterized in that the specific operation of the step (4) is to seal and put it in a 4° C. cold chamber.

The concentration of spores of *Monascus purpureus* is between $10^8$ pieces/mL to $10^{10}$ pieces/mL, and $10^9$ pieces/mL are preferred.

The production of spores suspension of *Monascus purpureus* were showed as follow:

(a) activation of strains: the PDA solid medium was used for strain activation, the activation time is twice, each time for 3 days.

(b) making suspension of spores: the sterilized distilled water is transferred to the solid medium in step (a), and the mycelium is scraped with inoculation ring to make the spores enter the distilled water, and then the spore suspension of *Monascus purpureus* can be obtained after filtration.

The strain of the invention belongs to *Monascus purpureus*, which was deposited in China General Microbiological Culture Collection Center (CGMCC) on Oct. 17, 2019, with the preservation number of CGMCC 18589.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
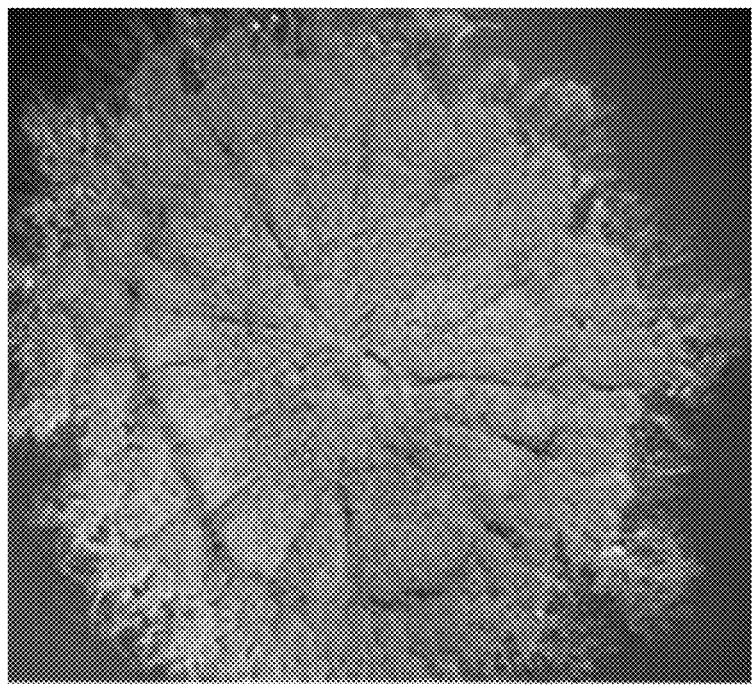
FIG. 1 The colony morphology of *Monascus purpureus*.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The invention is further described through some specific examples to better understand the invention, but it is only exemplary and does not constitute any limitation of the invention.

Example 1 Strain Screening

1. Screening of Original Strains

Some culture mediums were selected include potato glucose agar medium, MEA medium, wort medium, basic medium and liquid fermentation medium. The microbiological method was used to screen *Monascus purpureus*.

The specific steps are as follows.

(1) Sample Treatment

The mycelial micrograph of *Monascus purpureus* strain were taken from *Monascus* products such as red koji rice, red koji wine, red koji Toufu and other *Monascus* fermented products with an inoculation needle. The mycelial micrograph was grinded and then put into 90 mL sterile water, shaking at 200 r/min for 10 min at 30° C.

(2) Isolation and Purification of Strain

Under the aseptic operating condition, 1 mL of the supernatant of activation solution was added into a test tube containing 9 mL sterile water. After shaking, 1 mL of the supernatant was drawn from the test tube and added to another test tube which contains 9 mL of sterile water to obtain $10^{-1}$ diluent. According to this method, gradient dilutions of $10^{-2}$, $10^{-3}$, $10^{-4}$, $10^{-5}$ and $10^{-6}$ can be obtained. Take 100 μL diluent of each gradient, spread it evenly on the culture dish then mark it. The labeled plates were placed in the incubator at 30° C. for 3 days. The surface changes were recorded every day, and the strains conforming to the morphological characteristics of *Monascus* were selected for further purification and culture.

(3) Primary Screening and Rescreening

Plate coating method: Taking 200 μL diluent of each gradient, coating it evenly on the culture dish and labeled it. And then put the labeled plate in the mold incubator for 32° C. The culture and surface changes were recorded every day. After the third day, the suspected red colonies were selected and observed under a microscope.

Line separation method: After the observation of the suspicious colony in the initial screen plate, the strong colony was selected to be selected by the line inoculation method. After labeling, they were placed in a incubator at 31° C. for three days. After the first rescreening, the medium with strong and pure colony was selected to continue the screening process. The screening steps were repeated until no other miscellaneous bacteria appeared on the plate and the microscopic examination showed that there were no impurity bacteria. A pure strain was obtained by this method.

2. Identification Method

Observe the morphology of the above-mentioned colonies. A few *Monascus* spores was dipped by the inoculation ring, and inoculate them in the center of PDA sterile medium. After observe and record the colony morphology after 7 days at 25° C., the colony morphology was shown in FIG. 1. The individual morphology of colony was observed under the microscope after 7 days culturation. The result was as follows: the colony is bright red on the front and dark red on the back. The center of the colony has shown with compact texture and a little wrinkle. The connection between the colony and the culture medium is very close, which is hardly to separate. The edge of the colony is opaque and there are some white aerial hyphae and conidia can be found on it. The structure and color of the front and back sides of the colony, as well as the structure and color of the edge and center, are different.

Figure 2:
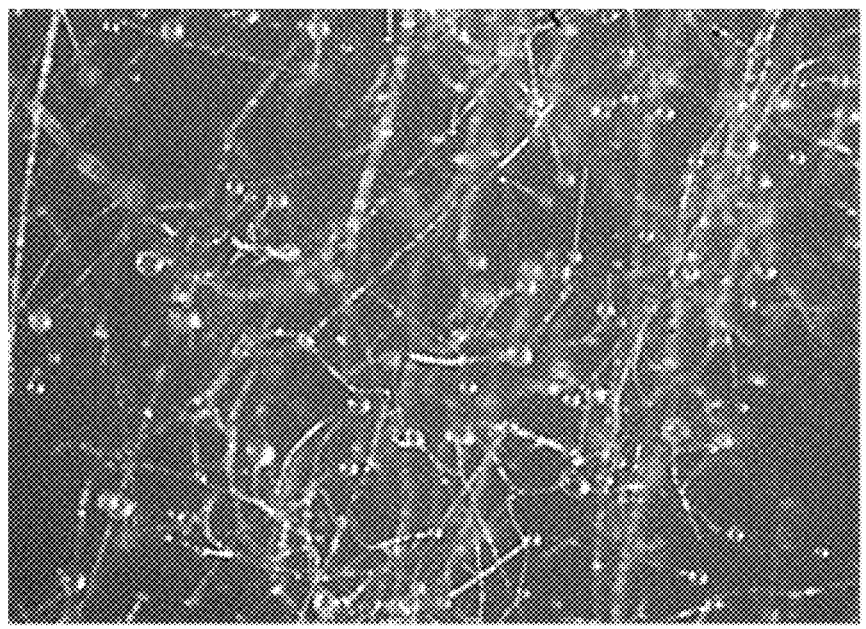
FIG. 2 The mycelial micrograph of *Monascus purpureus* strain.

It was found that a small number of mycelium balls were formed, and the mycelium balls were small and have short branches. After identification, the strain was identified as *Monascus purpureus*. The microscopic picture of mycelium was shown in FIG. 2.

Example 2 Mutation of Strain

1. Mutagenesis Method

The above-mentioned *Monascus* strains were irradiated and mutated by atmospheric and room temperature plasmas (ARTP). The strains were screened after primary screening and rescreening.

The mutation conditions of ARTP are shown in Table 1:

TABLE 1

| ARTP mutation conditions | |
|---|---|
| Parameter | Treatment conditions |
| Processing power/W | 120 |
| Processing distance/mm | 2 |
| Gas velocity/L · min$^{-1}$ | 10 |
| processing time/s | 90 |
| Sample size | 10 μL Spore suspension |

2. Screening of Mutagenic Strains

The spore suspension treated by irradiation was diluted with 0.9% sterile normal saline, and 100 μL of bacterial solution with three dilution gradients of $10^{-1}$, $10^{-2}$ and $10^{-3}$ was coated on the plate culture medium and cultured upside down at 30° C. for 3 days. The single colonies with obvious difference in colony morphology and faster growth or redder than the original strain were preliminarily screened and inoculated on the slope of the test tube for storage for the next experiment.

The screening method was as follows: inoculating different fermentation strains into cheese curd and then determining the content of ester compounds after 3 days of cultivation. Finally, a mutant strain of *Monascus purpureus* with high esters production activity was obtained. The strain was deposited in China General Microbiological Culture Collection Center (CGMCC) on Oct. 17, 2019, with the preservation number of CGMCC.18589.

Example 3 Preparation of *Monascus* Fermented Cheese

The mutation strain finally obtained in the second example were used to the production of *Monascus* fermented cheese.

1. The Preparation Technology of *Monascus purpureus* Spore Suspension.

(1) Activation the *Monascus purpureus* Strain with CGMCC No. 18589.

The purpose of this step is to improve the survival rate of spores extracted from the strain. The culture medium used was planar PDA solid medium, the culture temperature was 30° C. and activated twice for 3 days each time.

(2) Preparation of Spore Suspension:

10 mL sterilized distilled water was transferred onto the surface of each *Monascus* culture medium, and the surface of the colony was scraped by the inoculation ring to make the spores enter the distilled water. After a little stirring, the mycelium on the surface of the medium and the distilled water mixed with spores were filtered into a conical flask. The spore suspension was prepared and stored at 4° C.

(3) Spore Count:

Sterilized glass beads were added into the suspension and gently vibrated for 10 s. 1 mL suspension was taken in clean environment, and 99 mL sterilized distilled water was added to dilute 100 times. Use a pipette gun to absorb a small amount of suspension drops and add them on the counting area of blood cell counting board. After the spores settle, the numbers of spores were counted under the microscope. the spore concentration of $10^9$ spores/mL suspension was selected, and the calculation formula of spore concentration was as follows:

$$N = \frac{(n_1 + n_2 + n_3 + n_4 + n_5)}{80} \times 4 \times 10^6 \times 100$$

In the formula:

N—spore concentration, unit: one milliliter (/mL);

$N_{(1-5)}$—the number of spores in each calculation cell; dilution multiple.

2. The Processing Technology of *Monascus* Fermented Cheese.

(1) Cheese Processing:

The cheese curd was prepared with starter and chymosin. Then the cheese curd is cut into thin slices, and the vertical through holes are pricked on it with a 100 μL pipette gun. The number of perforations on each piece of cheese is 10.

(2) Transfer the Above-Mentioned Spores of *Monascus purpureus* on the Cheese Curd:

Spore suspension were injected into 4 selected holes in each slice, inject 5 μL suspension into each hole. Pay attention to don't overflow to the surface of cheese (the spore concentration is $10^9$/mL).

(3) Constant Temperature Culture:

The cheese cultivation temperature is 30° C., and the culture time is 3 days. After 3 days, the cheese sample was sealed and put into 4° C. cold chamber to mature for 1 month.

3. Analysis and Identification of Volatile Flavor Components in Cheese Sample

Figure 3:
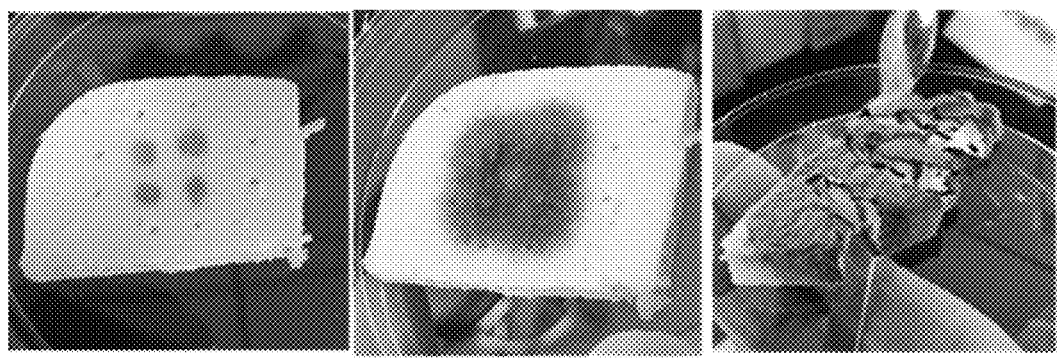
FIG. 3 The *Monascus* fermented cheese.
Figure 4:
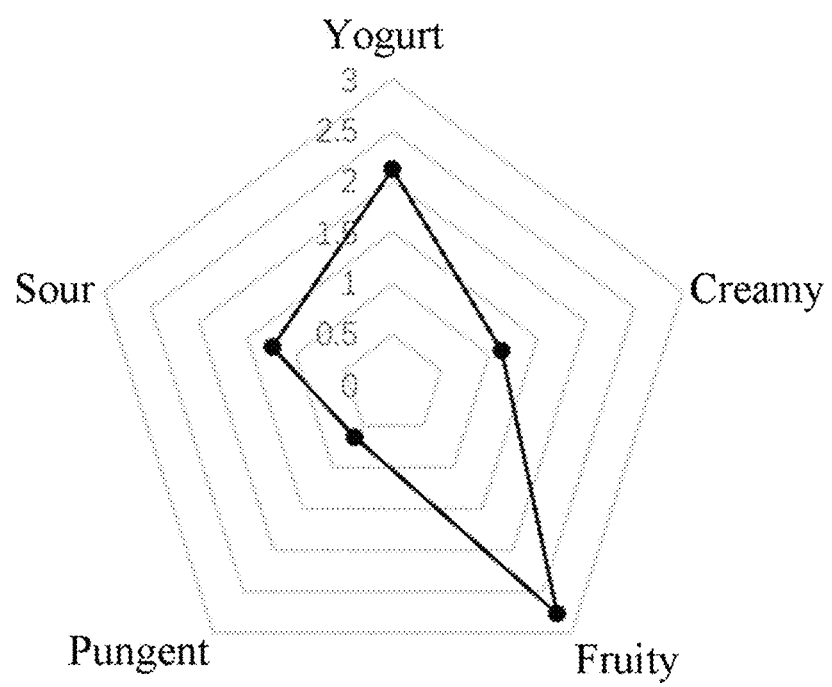
FIG. 4 The sensory evaluation and analysis of flavor profile of *Monascus* fermented cheese.

Gas chromatography mass spectrometry (GC-MS) was used to analyze and identify the volatile flavor components in the *Monascus* fermented cheese on the 1st, 5th, 9th, 17th and the final product (some are shown in FIG. 3). The results are as follows:

TABLE 2

| volatile flavor components of *Monascus* fermented cheese | | | | | |
|---|---|---|---|---|---|
| | Content (μg/kg) | | | | |
| Volatile Flavor Substances | D1 | D5 | D9 | D17 | Final Product |
| Alcohols | | | | | |
| 2-Heptanol | — | 39.33 | 170.29 | 16.33 | 32.40 |
| 2-Nonanol | — | 25.94 | 889.95 | 457.15 | 1635.85 |
| 2-Ethyl-1-hexanol | — | — | — | — | — |
| Benzyl alcohol | — | 158.08 | 2098.06 | — | — |
| Phenethyl alcohol | — | — | 4752.84 | 630.13 | — |
| Total Category | 0 | 3.00 | 4.00 | 3.00 | 2.00 |
| Total content | 0 | 223.35 | 7911.14 | 1103.61 | 1668.25 |
| Ketones | | | | | |
| 2,3-Butanedione | 71.48 | — | — | — | — |
| 2-Heptanone | 46.68 | 1319.32 | 7331.24 | 1923.78 | 274.43 |
| 2-Decanone | — | — | 216.42 | 264.39 | 996.10 |
| 2-Nonanone | — | 968.12 | 26755.79 | 26935.75 | 78525.85 |
| 2-Tridecanone | — | — | 1194.58 | 1623.31 | 8935.22 |
| 2-Pentadecanone | — | — | — | 14858.59 | 4522.91 |
| 2-Undecanone | — | 96.80 | 6843.52 | 8589.10 | 45422.22 |
| 2-Pentanone | — | — | 3619.25 | — | — |
| Acetoin | — | 8.95 | — | 7.81 | 247.15 |
| 3-Nonene-2-one | — | — | — | 63.63 | — |
| 3-Pentene-2-one | — | — | 533.47 | — | — |
| Total Category | 2.00 | 4.00 | 7.00 | 8.00 | 7.00 |
| Total content | 118.16 | 2393.21 | 46494.27 | 54266.35 | 138923.88 |
| Esters | | | | | |
| 3-Methyl-5-pentanolactone | — | — | 721.07 | 800.84 | 56270.88 |
| Ethyl 3-hydroxyhexanoate | — | — | 1169.26 | 216.28 | — |
| γ-Nonanolactone | — | — | 278.90 | — | — |
| γ-Octalactone | — | — | 610.97 | 1029.32 | 2650.34 |
| Butyl butyrate | — | — | — | 360.79 | 393.45 |
| Heptyl butyrate | — | — | 35.11 | 166.73 | 466.71 |
| Hexyl butyrate | — | — | 4059.80 | 867.95 | 867.95 |
| Isoamyl butyrate | — | 251.46 | — | 565.90 | 769.90 |
| δ-Decalactone | — | — | 1222.54 | 730.58 | — |
| Ethyl heptanoate | — | 109.55 | 2665.51 | 558.51 | 683.51 |
| Butyl decanoate | — | — | 434.00 | 878.30 | 4380.55 |
| Methyl decanoate | — | — | 126.93 | 72993.74 | — |
| Ethyl decanoate | — | 1299.53 | 192805.84 | — | 20656.21 |
| Isobutyl decanoate | — | — | 2050.37 | 1287.52 | — |
| N-propyl decanoate | — | — | 461.09 | 165.83 | — |
| n-Propyl hexanoate | — | 69.86 | 8.88 | 737.45 | — |
| Butyl hexanoate | — | — | 3193.11 | — | 8083.48 |
| Hexyl hexanoate | — | — | 1544.60 | 840.80 | 2630.77 |
| Amyl hexanoate | — | — | 343.30 | 615.47 | 1467.68 |
| Isobutyl hexanoate | — | 1223.10 | 5493.55 | 2721.82 | — |
| Isopentyl hexanoate | — | 455.73 | 5780.12 | 3385.30 | 9970.70 |
| Ethyl nonanoate | — | — | 5576.85 | 2256.28 | 3356.78 |
| Whiskey lactone | — | — | — | 242.03 | — |
| Propyl octanoate | — | — | 648.60 | 219.61 | — |
| Methyl octanoate | — | — | 351.47 | 346.00 | 335.33 |
| Ethyl octanoate | — | 3131.87 | 171439.31 | 42919.59 | 82584.59 |
| Isobutyl octanoate | — | 125.12 | 3980.35 | 1594.46 | — |
| Isoamyl octanoate | — | 34.01 | 1620.80 | 875.48 | — |
| N-butyl octanoate | — | — | 985.12 | 1293.10 | — |
| Isoamyl nitrite | — | — | 158.29 | 72.26 | — |
| 1-Monobutyrin | — | — | 14497.44 | 1676.93 | — |
| Heptyl acetate | — | 22.53 | 279.03 | 1050.16 | 1950.22 |
| Butyl isobutyrate | — | — | 228.46 | — | — |
| Ethyl caproate | — | 6286.25 | 59854.17 | 12055.94 | — |
| Total Category | — | 11.00 | 31.00 | 30.00 | 17.00 |
| Total content | — | 13009.02 | 482624.82 | 153524.98 | 197519.05 |
| Aldehydes | | | | | |
| 3-Hydroxybutyraldehyde | 11.43 | — | — | — | — |
| Benzaldehyde | 528.33 | 1173.04 | — | 753.59 | 365.04 |
| Heptanal | 37.01 | — | — | — | — |
| Decanal | 26.51 | — | 247.31 | 113.22 | — |
| Pentanal | 2.07 | — | — | — | — |

TABLE 2-continued volatile flavor components of *Monascus* fermented cheese

| Volatile Flavor Substances | Content (μg/kg) | | | | |
|---|---|---|---|---|---|
| | D1 | D5 | D9 | D17 | Final Product |
| 3-Methyl butanal | 9.88 | — | — | — | — |
| Hexanal | 8.29 | — | — | — | — |
| Octanal | 5.24 | — | — | — | 1.26 |
| Total Category | 7.00 | 1.00 | 1.00 | 2.00 | 2.00 |
| | | | | | |
| Total content | 628.76 | 1173.04 | 247.31 | 866.81 | 366.40 |
| Fatty acids | | | | | |
| | | | | | |
| 2-Methylhexanoic acid | — | — | 178.22 | 262.31 | 36780.16 |
| 9-Decenoic acid | — | — | 9798.08 | 10845.37 | 15683.57 |
| Acetic acid | 4095.94 | 67.48 | 2695.73 | 6287.95 | 69181.42 |
| Butanoic acid | — | — | 100985.72 | 121601.82 | 948159.56 |
| Heptanoic acid | — | — | 5029.21 | 6416.33 | — |
| Decanoic acid | — | — | 124053.55 | 117672.77 | 480871.01 |
| Hexanoic acid | 913.90 | 1335.07 | 220599.14 | 198861.82 | 1049740.9 |
| Nonanoic acid | — | — | 3542.55 | 4430.70 | 19235.20 |
| Myristic acid | — | — | 7418.54 | 7384.24 | 29836.14 |
| Undecanoic acid | — | — | 827.11 | 758.31 | — |
| Octanoic acid | 444.53 | 487.70 | 171399.09 | 163988.58 | 719504.04 |
| Isobutyric acid | — | — | 100.58 | 162.70 | — |
| Lauric acid | — | — | 29475.67 | 29524.86 | 121530.61 |
| Pentanoic acid | — | — | 1921.18 | 3080.05 | 30497.78 |
| Total Category | 3.00 | 3.00 | 14.00 | 14.00 | 12.00 |
| | | | | | |
| Total content | 5454.37 | 1890.25 | 678024.39 | 671277.81 | 3521020.3 |
| Aromatic and heterocyclic | | | | | |
| | | | | | |
| 2,3,5,6-Tetramethylpyrazine | — | — | — | 412.44 | 6003.74 |
| 2,3,5-Trimethylpyrazine | — | — | 45.86 | 239.79 | 3749.06 |
| 2,3-Dimethylpyrazine | — | — | — | 39.87 | 43.66 |
| 2'-Deoxycytosine nucleoside | — | — | — | 253.68 | 158.23 |
| 2-Ethyl-6-methylpyrazine | — | — | — | 181.77 | 293.33 |
| Styrene | — | 148.45 | 6977.65 | 4613.93 | 9824.55 |
| Total Category | 0 | 1.00 | 2.00 | 6.00 | 6.00 |
| | | | | | |
| Total content | — | 148.45 | 7023.51 | 5741.49 | 20072.57 |

The results of GC-MS were analyzed and compared. The results are shown in table 2. A total of 82 volatile flavor compounds were detected in *Monascus* fermented cheese. Compared with the normal cheese processing. the types and contents of ester compounds in *Monascus* fermented cheese are very high, as well as the fatty acids (3521020.3 m/kg). And each kind of compound in Table 2 are discussed as follow:

(1) Fatty Acids

Fatty acids (acetic acid, butanoic acid, hexanoic acid and octanoic acid) are important, or even dominating, components of the flavor of many cheese types. They also serve as precursors of methyl ketones, alcohols, lactones and esters. Based on Table 2, the contents of caproic acid, octanoic acid, butyric acid and decanoic acid was gradually increasing during the storage time. Among these fatty acids, caproic acid (1049740.9 μg/kg) have a strong milk rancid odor for its low threshold (less than 0.3 mg/mL). While octanoic acid has a rancid smell, butyric acid has a pungent flavor, and decanoic acid has unpleasant fat smell. All of these four fatty acids give cheese a specific rancid butter flavor, which have a great impact on the flavor profile of cheese.

(2) Ester Compounds:

Esters are a common class of flavor compounds in cheese. Esterification reactions occur between short- to medium-chain fatty acids and primary and secondary alcohols derived from lactose fermentation or from amino acid catabolism. Especially ethyl esters are known for their important role in the formation of a fruity character in cheese. According to Table 2, the contents of ester compounds detected in the *Monascus* fermented cheese ripening time showed an gradually rising state. The total content of ester compounds in *Monascus* fermented cheese is 197519.05 μg/kg, and among them there are many ethyl esters, such as ethyl caproate (Brandy flavor) and ethyl decanoate (fruity flavor). These ethyl esters have a strong pleasant wine or fruity aroma. Therefore, the *Monascus* fermented cheese have a unique pleasant flavor.

(3) Ketones

Ketones and aldehydes are relatively active and unstable intermediates, which can be converted into alcohols or fatty acids under certain conditions. Ketones, especially the methyl ketones are common constituents of most dairy products, they are the key flavor compounds in ultra-high temperature sterilized milk and Blue cheese. They can contribute the yogurt and cream flavor to dairy products, which could also greatly improve the flavor profile of cheese. The methyl ketones contents in the *Monascus* fermented cheese were also very high, especially the 2-nonanone, 2-decanone, 2-pentanone and 2-undecanone, they provide strong creamy flavor to the cheese.

(4) Other Compounds

There were still have some alcohols, aldehydes, aromatic and heterocyclic compounds in *Monascus* fermented cheese. Compared with the fatty acids, esters and ketones, the contents of these compounds were not very high. They may give little effect on the flavor profile of *Monascus* fermented cheese.

Analysis of Flavor Profile Characteristics in Sensory Evaluation

According to the description characteristics of cheese flavor, the flavor profile characteristics of Monascus fermented cheese were analyzed by using a 0-3 scale (0=not detected; 1=extremely weak odor; 2=clear odor; 3=intense odor) with seven possible scores (half values allowed). The results are shown in FIG. 3. It can be seen from the figure that the Monascus fermented cheese mainly has fruity, yogurt flavor, slightly cream flavor, sour taste and milk rancid odor. The prominent fruity and slight koji flavor in cheese mainly comes from ester compounds, which can change the overall flavor profile of cheese. While the prominent flavor similar to yogurt and creamy in cheese comes from methyl ketones, such as 2-nonanone, 3-hydroxy-2-butanone. The sour smell of cheese were comes from acetic acid. The pungent flavor are come from the fatty acids, such as butyric acid. The results of sensory evaluation of Monascus fermented cheese were similar to those of GC-MS, which indicated that these odors could well describe the flavor characteristics of Monascus fermented cheese.

It can be seen from the above that the Monascus purpureus strain with high ester producing activity can synthesis esters, fatty acids and methyl ketones with high contents in cheese product. So that the Monascus fermented cheese has a strong fruit and milk flavor, and can significantly improve the quality of cheese. The new ester flavor Monascus cheese should be more in line with the taste of Chinese people.

DEPOSIT OF BIOLOGICAL MATERIAL

The following biological material has been deposited under the terms of the Budapest Treaty with the China General Microbiological Culture Collection Center (CGMCC), Institute of Microbiology, Chinese Academy of Sciences, 3 Beichen West Road, Chaoyang District, Beijing, China, 100101, and given the following number:

| Deposit | Accession Number | Date of Deposit |
|---|---|---|
| Monascus purpureus | CGMCC No. 18589 | Oct. 17, 2019 |

The strains have been deposited under conditions that assure that access to the culture will be available during the pendency of this patent application to one determined by the Commissioner of Patents and Trademarks to be entitled thereto under 37 C.F.R. § 1.14 and 35 U.S.C. § 122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by government action.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A high-esters producing activity strain of *Monascus purpureus*, having been deposited on Oct. 17, 2019 in China General Microbiological Culture Collection Center (CGMCC), with the accession number of CGMCC 18589, that can synthesize esters, fatty acids and methyl ketones with high contents in cheese product.

2. The high-esters producing activity strain of *Monascus purpureus* according to claim 1, the strain of *Monascus purpureus* having been applied as the adjunct culture in *Monascus*-fermented cheese.

3. A production process of *Monascus*-fermented cheese, which is characterized by the following steps:
   (1) preparation of the cheese curd with starter and chymosin;
   (2) inoculation with spores of *Monascus purpureus* with high-esters producing activity according to claim 1;
   (3) keeping the cheese curd at a constant temperature to make the *Monascus* grow better;
   (4) cheese ripening.

4. The production process of *Monascus*-fermented cheese according to claim 3, the production process of *Monascus*-fermented cheese having included cutting the cheese curd into thin slices and penetrating the curd to form vertical holes.

5. The production process of *Monascus*-fermented cheese according to claim 4, which is characterized in that the specific operation of step 2) is to prepare a suspension of the spores of *Monascus purpureus* with high-esters producing activity and then inject it into the hole.

6. The production process of *Monascus*-fermented cheese according to claim 4, which is characterized in that the constant cultivation temperature of step 3 is 25-35° C., and the cultivation time is 2-4 days.

7. The production process of *Monascus*-fermented cheese according to claim 4, which is characterized in that the specific operation of step 4 is to put the cheese in a 4° C. chamber to mature.

8. The production process of *Monascus*-fermented cheese according to claim 4, which is characterized in that in step 2, the spores of *Monascus purpureus* with high esters production is made into a suspension, the preferred concentration being $10^8$ pieces/mL to $10^{10}$ pieces/mL.

9. The production process of *Monascus*-fermented cheese according to claim 8, which is characterized in that the specific steps for producing a spore suspension of *Monascus purpureus* with high-esters producing activity were as followed:
   (a) activation of strains: PDA solid medium was used for strain activation, activated twice, each time for 3 days, and
   (b) making suspension of spores: the sterilized distilled water was transferred to the solid medium, and the mycelium was scraped with a inoculation ring to dislodge the spores into the distilled water, and then the spore suspension was obtained after filtration.

* * * * *